(12) United States Patent
Hsu

(10) Patent No.: US 11,998,498 B2
(45) Date of Patent: Jun. 4, 2024

(54) REMOTE CONTROL FOR SICKBED

(71) Applicant: SHANGHAI YONGSHUNDA MEDICAL EQUIPMENT CO., LTD, Rugao (CN)

(72) Inventor: Cheng-Hung Hsu, New Taipei (TW)

(73) Assignee: SHANGHAI YONGSHUNDA MEDICAL EQUIPMENT CO., LTD, Shanghai (CN)

( * ) Notice: Subject to any disclaimer, the term of this patent is extended or adjusted under 35 U.S.C. 154(b) by 464 days.

(21) Appl. No.: 17/503,330

(22) Filed: Oct. 17, 2021

(65) Prior Publication Data

US 2023/0121951 A1  Apr. 20, 2023

(51) Int. Cl.
*A61G 7/018* (2006.01)
*A61G 7/05* (2006.01)
*G08B 3/10* (2006.01)
*G08C 17/02* (2006.01)
*G16H 40/67* (2018.01)
*H04W 4/80* (2018.01)

(52) U.S. Cl.
CPC .......... *A61G 7/018* (2013.01); *A61G 7/0524* (2016.11); *G08B 3/1008* (2013.01); *G08C 17/02* (2013.01); *G16H 40/67* (2018.01); *H04W 4/80* (2018.02); *A61G 2203/12* (2013.01); *G08C 2201/30* (2013.01)

(58) Field of Classification Search
None
See application file for complete search history.

(56) References Cited

U.S. PATENT DOCUMENTS

| | | | | |
|---|---|---|---|---|
| 8,327,160 B2 * | 12/2012 | Sakamoto | ............ | G08C 17/02 713/300 |
| 8,533,878 B2 * | 9/2013 | Wu | .......... | A61G 7/08 5/616 |
| 2010/0037082 A1 * | 2/2010 | Sakamoto | ............ | G08C 17/02 713/502 |

* cited by examiner

*Primary Examiner* — Carlos Garcia
(74) *Attorney, Agent, or Firm* — PAI PATENT & TRADEMARK LAW FIRM; Chao-Chang David Pai

(57) ABSTRACT

A remote control for a sickbed contains: a body, a calling assembly, an operational panel, and a switch. The body includes a power supply set, a microcontroller, a calling knob, and a wireless communication module. The operational panel includes multiple buttons so that when pressing any one of the multiple buttons, the microcontroller starts the transmission mechanism to actuate the sickbed to lift or descend. The switch is arranged on the body and moves close to or away from the calling knob. When the switch is pushed to abut against the calling knob, the calling knob is maintained on a locking position and does not generate a calling signal. When the switch is pushed to move away from the calling knob, the calling knob is maintained on a starting position and is pressed to conduct the power and to send the calling signal.

10 Claims, 9 Drawing Sheets

REMOTE CONTROL FOR SICKBED

FIELD OF THE INVENTION

The present invention relates to a remote control, and more particularly to the remote control for a sickbed which has calling effect and communication capacity.

BACKGROUND OF THE INVENTION

A conventional sickbed or medical bed for hospital or rehabilitation, pension contains a one-touch call bell in a large size, so a remote control is provided to control an angle of the sickbed or the medical bed.

However, the remote control cannot be used to call medical personnel urgently.

In addition, the call bell and the remote control are independent components of the sickbed or the medical bed which have to equip with an independent power supply respectively in different accommodation spaces. Also, patients are not easy to distinguish during emergency use, and the remote control is operated inconveniently, and the sickbed cannot provide instant safety care and monitoring.

The present invention has arisen to mitigate and/or obviate the afore-described disadvantages.

SUMMARY OF THE INVENTION

The primary objective of the present invention is to provide a remote control for a sickbed which is capable of calling caregiver easily and wirelessly by way of the calling knob, the switch, and the care monitoring APP program built in the mobile, thus achieving smart calling and communication among the user, the caregiver, and the user's families.

To obtain the above objective, a remote control for a sickbed provided by the present invention, the sickbed including a holding plate and a transmission mechanism. The remote control is electrically connected with the transmission mechanism to control the holding plate to lift or descend, and the remote control communicates with a remote management platform wirelessly.

The remote control contains: a body, a calling assembly, an operational panel, and a switch.

The calling assembly received in the body and including a power supply set, a microcontroller unit, a calling knob, and a wireless communication module which are electrically connected, wherein the microcontroller unit drives and controls the holding plate to lift or descend in a programmable editing manner, the calling knob generates a calling signal, and the calling signal is sent to the remote management platform via the wireless communication module.

The operational panel is located on the body and includes multiple buttons electrically connected with the microcontroller. When pressing any one of the multiple buttons, the microcontroller starts the transmission mechanism to actuate the holding plate to lift or descend.

The switch is arranged on the body and moves close to or away from the calling knob. When the switch is pushed to abut against the calling knob, the calling knob is maintained on a locking position and does not generate the calling signal. When the switch is pushed to move away from the calling knob, the calling knob is maintained on a starting position and is pressed to conduct the power and to send the calling signal.

DETAILED DESCRIPTION OF THE PREFERRED EMBODIMENTS

Figure 10:
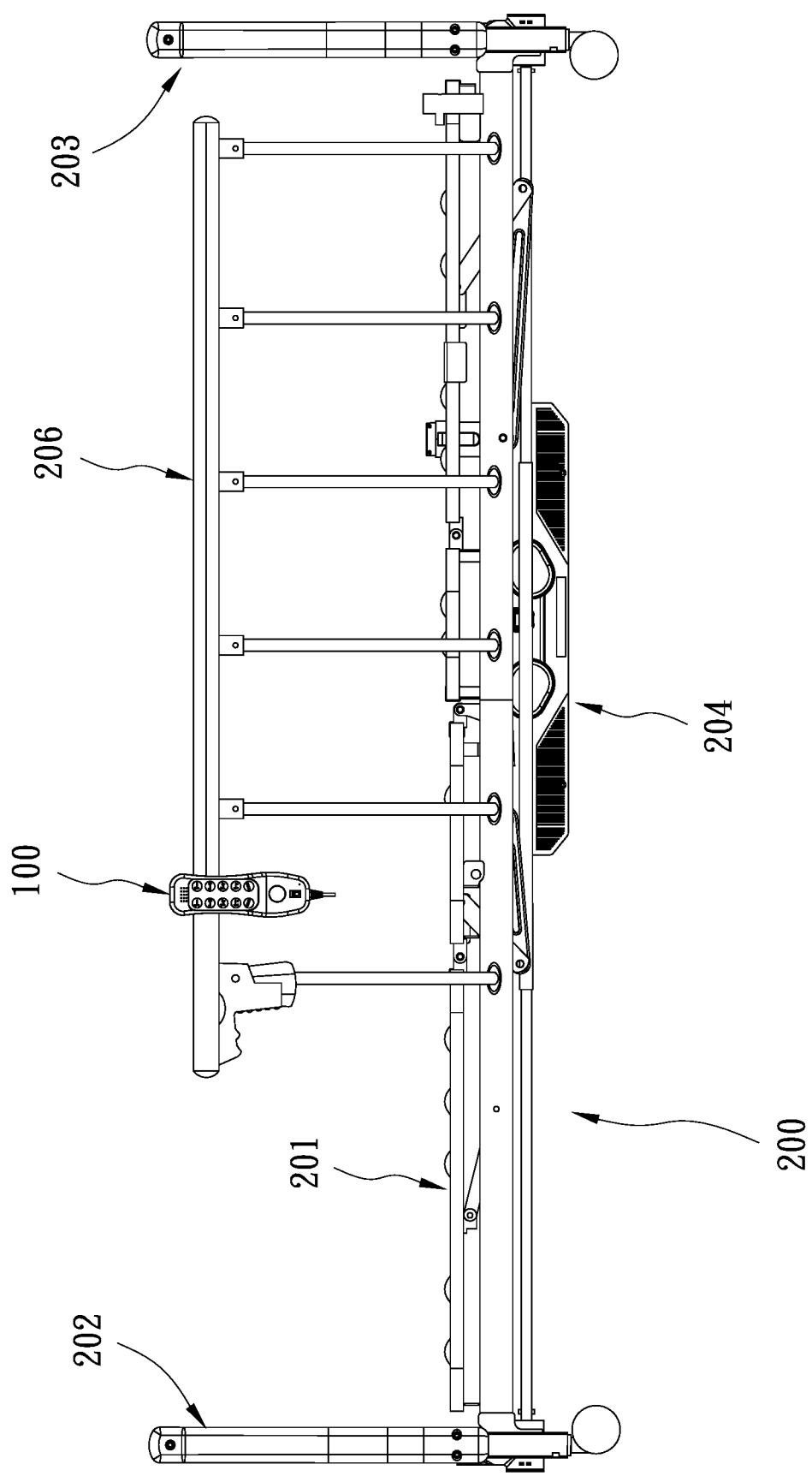
FIG. 10 is a side plan view showing the application of the remote control for the sickbed according to the preferred embodiment of the present invention.

With reference to FIG. 10, a remote control 100 for a sickbed according to a preferred embodiment of the present invention, the sickbed 200 comprises a holding plate 201, a head mounting 202, a bed end 203, and a transmission mechanism 204. The remote control 100 is electrically connected with the transmission mechanism 204 to control the holding plate 201, the head mounting 202, and the bed end 203 to lift or descend. In this embodiment, a power of the transmission mechanism 204 comes from supply mains, and the transmission mechanism 204 is disclosed in U.S. Pat. No. 8,533,878.

Figure 1:
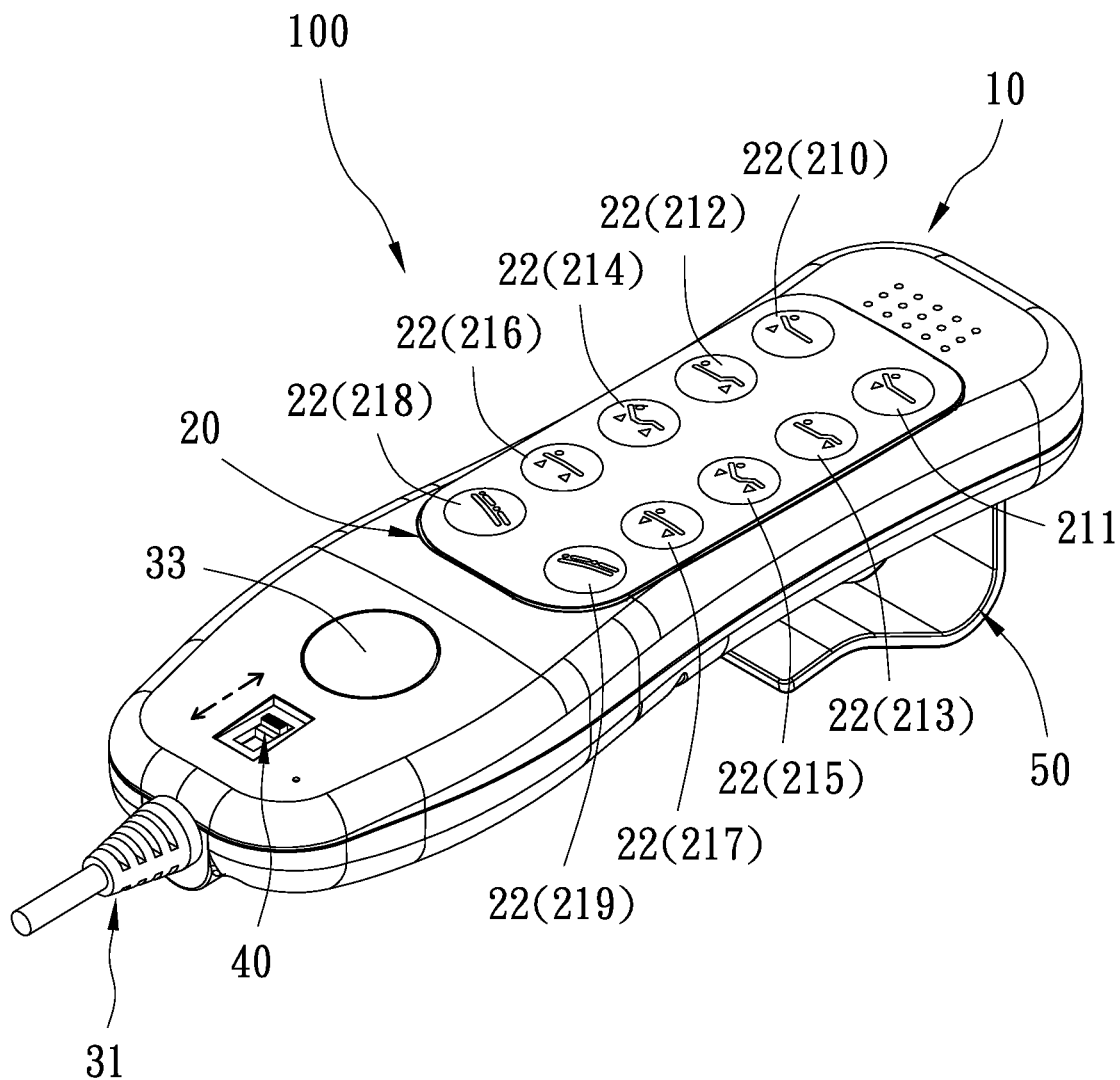
FIG. 1 is a perspective view showing the assembly of a remote control for a sickbed according to a preferred embodiment of the present invention.
Figure 2:
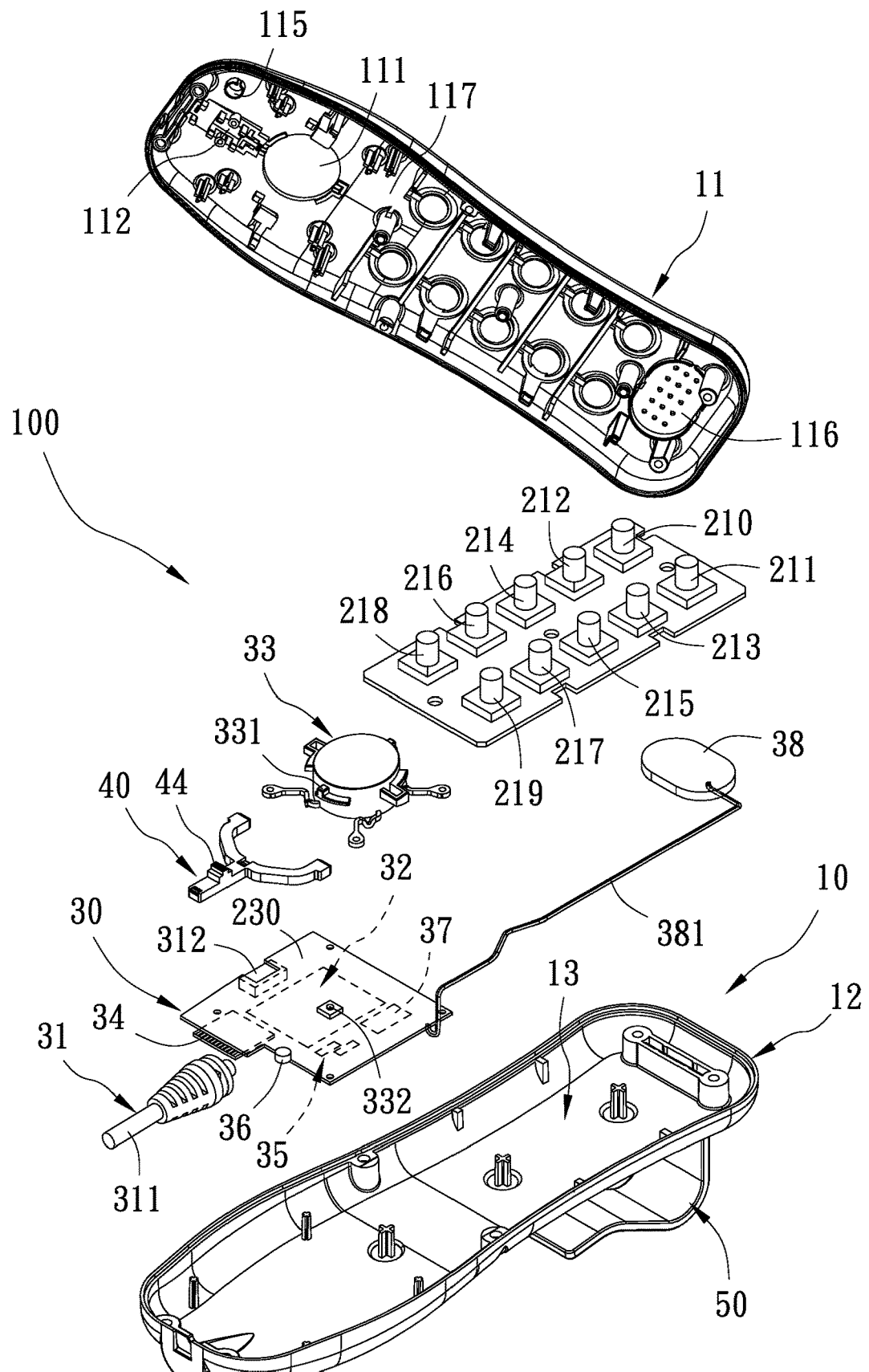
FIG. 2 is a perspective view showing the exploded components of the remote control for the sickbed according to the preferred embodiment of the present invention.

Referring to FIGS. 1 and 2, the remote control 100 includes a body 10, an operational panel 20, a calling assembly 30, a switch 40, and a hook 50.

Figure 3:
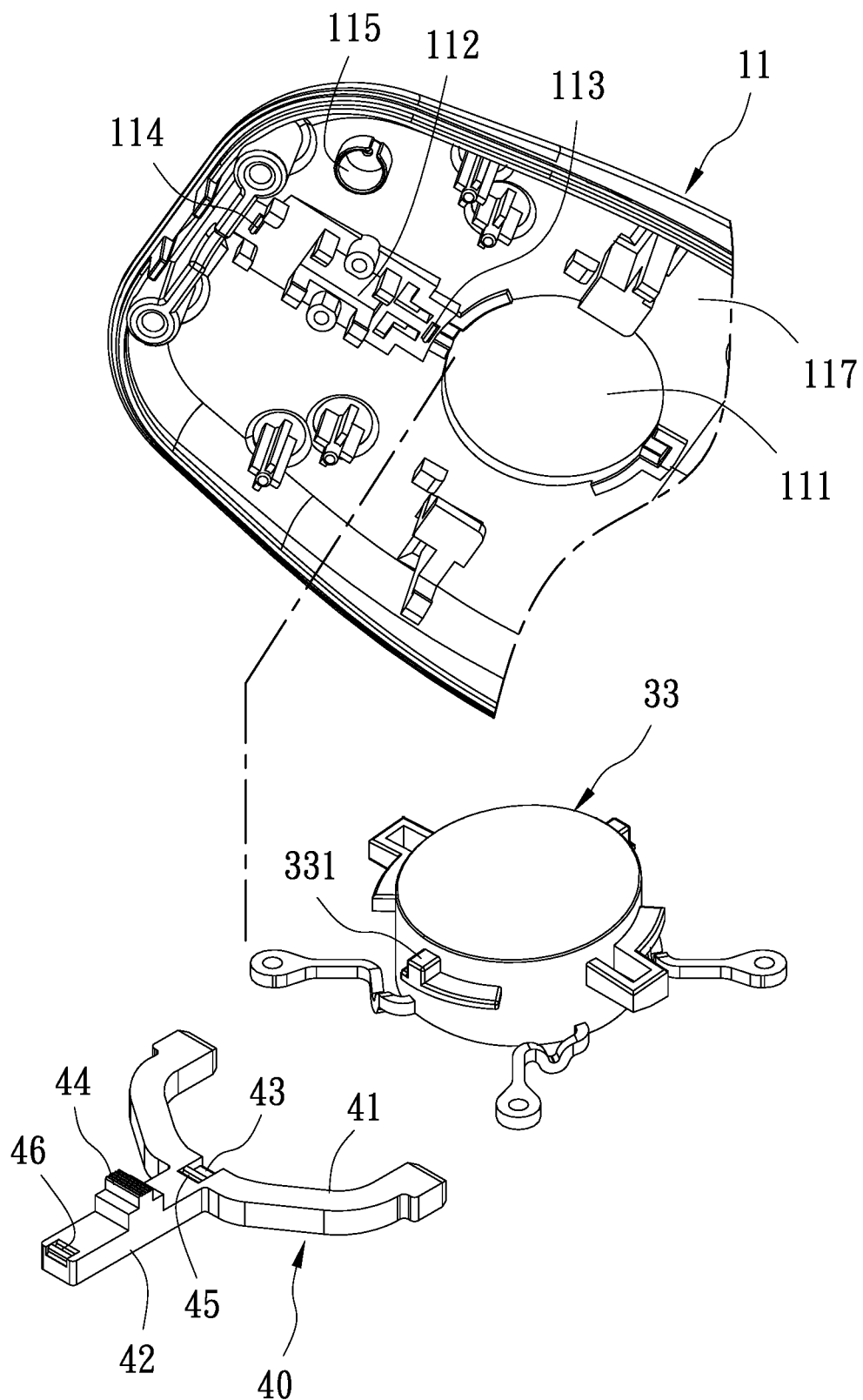
FIG. 3 is a perspective view showing the assembly of a part of the remote control for the sickbed according to the preferred embodiment of the present invention.

As shown in FIGS. 2 and 3, the body 10 includes a first casing 11, a second casing 12 connected with the first casing 11, and an accommodation chamber 13 defined between the first casing 11 and the second casing 12. The first casing 11 has a circular shape of first orifice 111 defined on a first end thereof, an elongated shape of second orifice 112 formed beside the first orifice 111, a first engagement portion 113 and a second engagement portion 114 which are formed on two sides of the second orifice 112, a first defining groove 115 defined adjacent to the first end of the first casing 11, and a second defining groove 116 formed proximate to a second end of the first casing 11 and away from the first defining groove 115. The first engagement portion 113, the second engagement portion 114, the first defining groove 115, and the second defining groove 116 are located on an inner fringe 117 of the first casing 11. The first orifice 111 and the second orifice 112 communicate with the accommodation chamber 13. In this embodiment, the first engagement portion 113 and the second engagement portion 114 are an arcuate protrusion.

Figure 7:
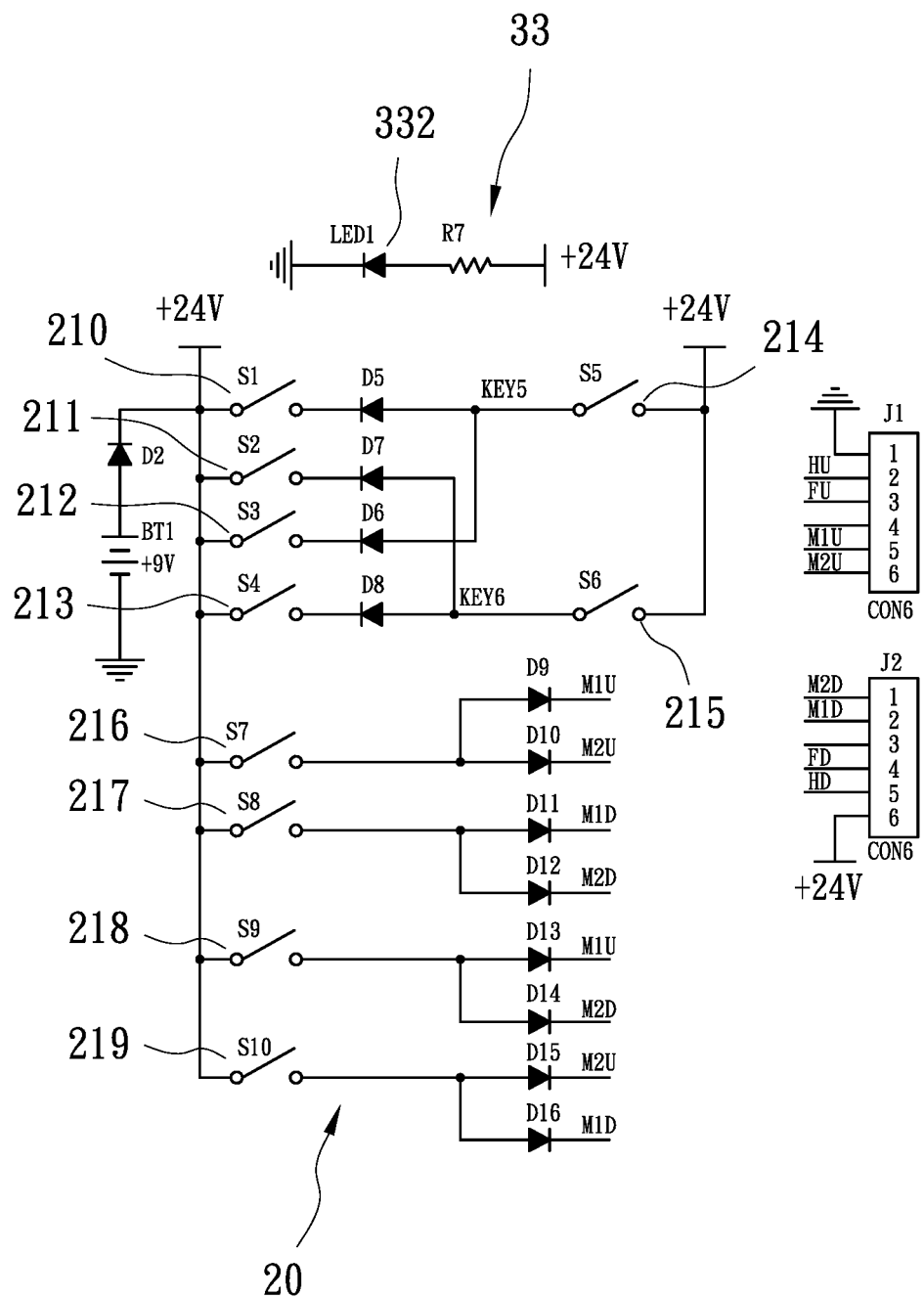
FIG. 7 is a circuit diagram of an operational panel and the calling knob of the remote control for the sickbed according to the preferred embodiment of the present invention.

With reference to FIG. 7, the operational panel 20 is located on a middle section of the body 10. The operational panel 20 includes multiple buttons 210 to 219 and a touch film 22 corresponding to the multiple buttons 210 to 219.

Figure 5:
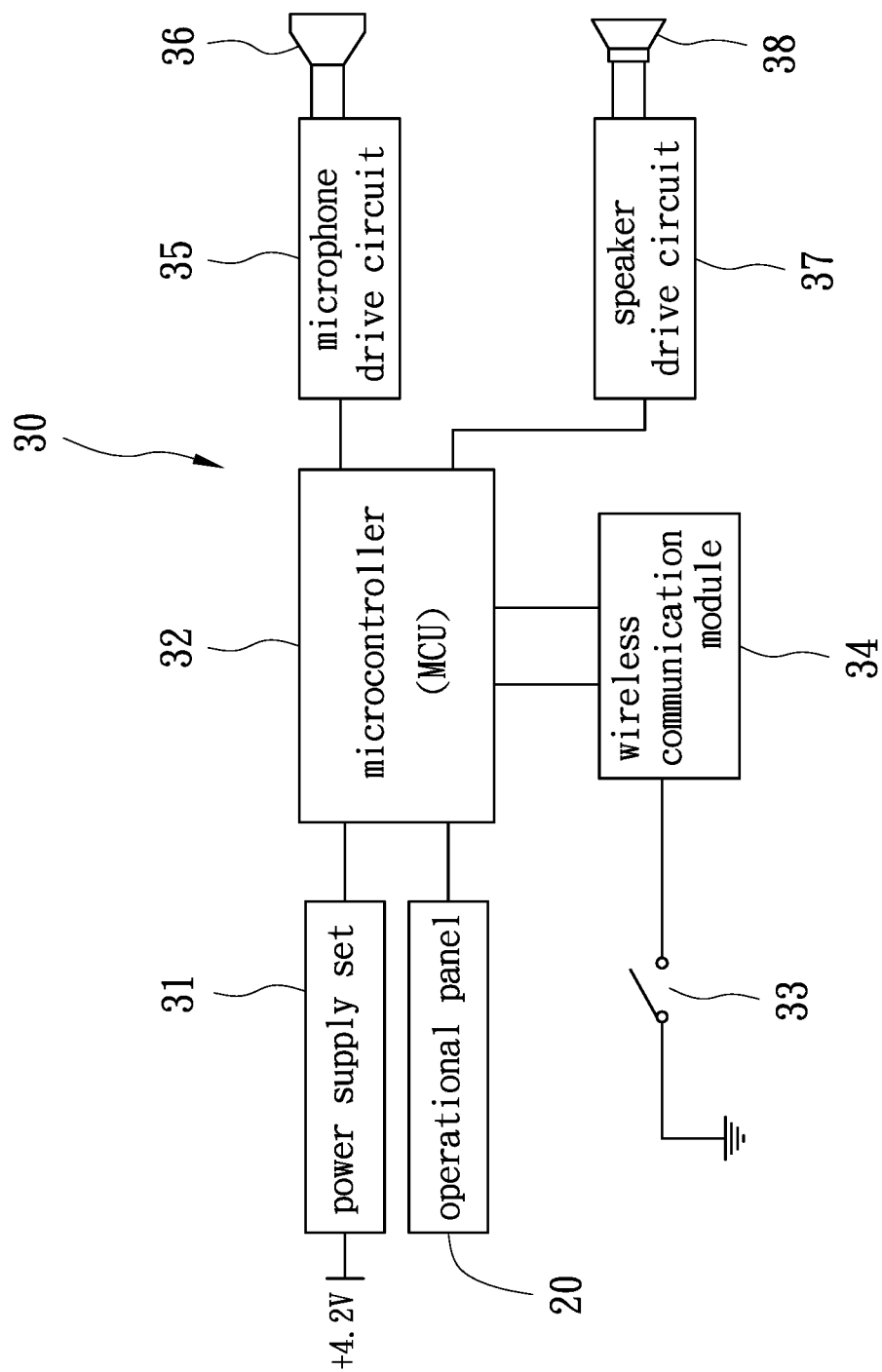
FIG. 5 is a block circuit diagram of a calling assembly of the remote control for the sickbed according to the preferred embodiment of the present invention.

Referring to FIGS. 2 and 5, the calling assembly 30 is received in the body 10 and includes a power supply set 31, a microcontroller 32, a calling knob 33, a wireless communication module 34, a microphone drive circuit 35, a microphone 36, a speaker drive circuit 37, and a speaker 38.

Figure 4:
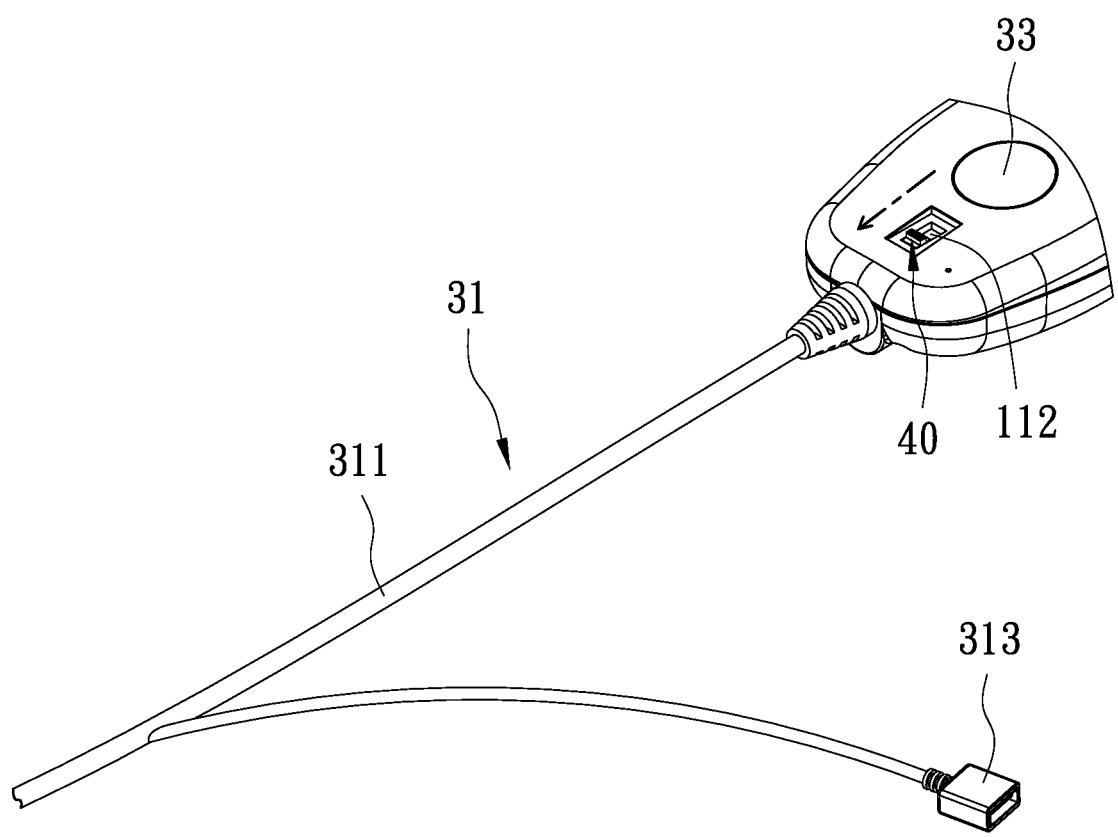
FIG. 4 is another perspective view showing the assembly of a part of the remote control for the sickbed according to the preferred embodiment of the present invention.

The power supply set 31 has a power cable 311 and a lithium battery 312 electrically connected with the microcontroller 32. In this embodiment, the lithium battery 312 is a 9V (voltage) battery. The power cable 311 is connected with the transmission mechanism 204 so that supply mains is supplied to the controller 100 from the transmission mechanism 204 via the power cable 311, and the supply mains is stored in the lithium battery 312, thus providing backup power when the supply mains is failed. As shown in FIG. 4, the power supply set 31 has a USB connector 313 configured to connect with the power cable 311 parallelly when the supply mains is failed or the sickbed is moved temporarily outside. Furthermore, other powers are supplied to the controller 100 from external equipment (such as a mobile power pack) via the USB connector 313.

Figure 6:
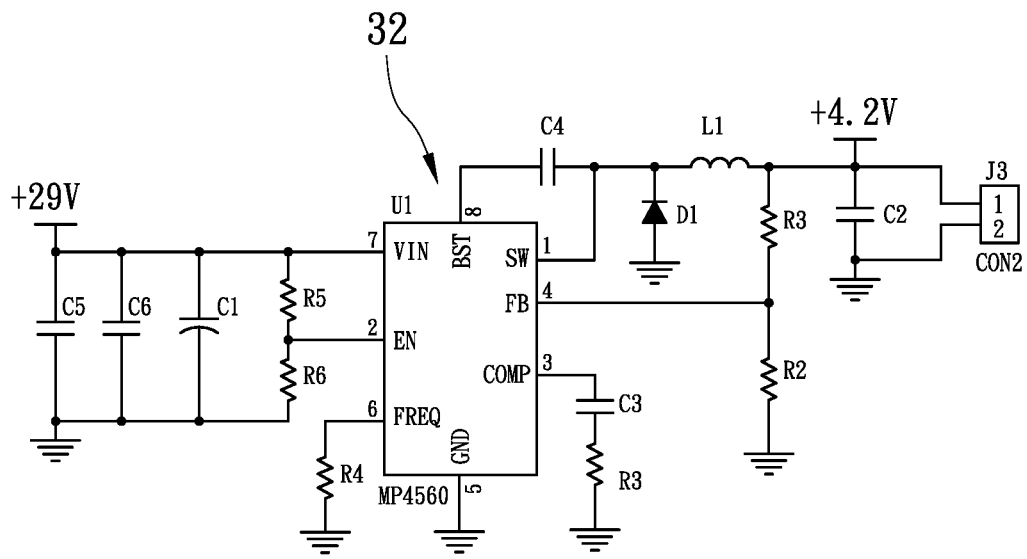
FIG. 6 is a circuit diagram of a microcontroller of the remote control for the sickbed according to the preferred embodiment of the present invention.

As illustrated in FIG. 6, the microcontroller 32 drives and controls the holding plate 201 to lift or descend in a programmable editing manner, and executing a calling signal generated by the calling knob 33, and the calling signal is sent to a remote management platform 310 via the wireless communication module 34. In this embodiment, the microcontroller 32 is arranged on a circuit substrate 320, and a MP4560 chip is applicable.

With reference to FIGS. 2 and 7, the calling knob 33 flexibly extending out of the first orifice 111 of the body 10. In this embodiment, a locking projection 331 is located beside the calling knob 33, and a display lamp 332 is arranged in the calling knob 33 so that the display lamp 332 emits lights to provide instruction after the calling knob 33 is pressed.

The wireless communication module 34 is a wireless router or wireless network card so as to send the calling signal wirelessly, wherein the wireless router sends the calling signal in a protocol manner by using a router (such as 802.11ax or 802.11ac wave2) of Wi-Fi. Alternatively, the wireless communication module 34 sends the calling signals by using Bluetooth in 2.4 GHz to 2.485 GHz. In addition, a signal exchanger 300 is configured to support the Wi-Fi or the Bluetooth so as to communicate the calling signals between the controller 100 and the remote management platform 310.

Referring further to FIGS. 5 and 6, the microphone drive circuit 35 is electrically connected between the microcontroller 32 and the microphone 36, wherein the microphone 36 is accommodated in the defining groove 115 of the first casing 11. In this embodiment, the microphone 36 is a condenser microphone.

Figure 8:
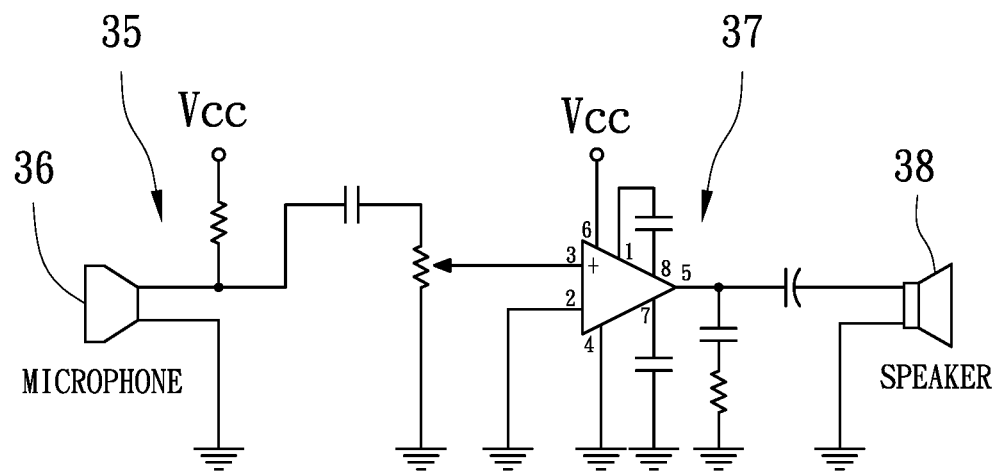
FIG. 8 is a circuit diagram of a speaker drive circuit and a microphone drive circuit of the remote control for the sickbed according to the preferred embodiment of the present invention.

As shown in FIG. 8, the speaker drive circuit 37 is electrically connected between the microcontroller 32 and the speaker 38. In this embodiment, the speaker drive circuit 37 has a LM386 chip and is configured to amplify audio.

The speaker 38 is received in the second defining groove 116, as shown in FIG. 2, and the speaker 38 is oval and is an internal magnetic miniature loudspeaker, wherein the speaker 38 is connected with the speaker drive circuit 37 and the microcontroller 32 via a guide wire 381.

The switch 40 is arranged on the body 10 and in a Y shape, wherein the switch 40 includes a U-shaped extension 41 fitted on a side of the calling knob 33, a straight extension 42 located beside the U-shaped extension 41, a fixing trench 43 defined on a center of the U-shaped extension 41, a protruded portion 44 extending from the straight extension 42 and out of the second orifice 112 of the body 10, and a first connection portion 45 and a second connection portion 46 which are located beside the protruded portion 44. The first connection portion 45 and the second connection portion 46 are an arcuate recess. A size of the protruded portion 44 of the switch 40 is less than a size of the second orifice 112 so that the protruded portion 44 is pushed along the second orifice 112, and the switch 40 is moved linearly when close to or away from the calling knob 32.

The hook 50 is arranged on a side of the second casing 12 of the body 10 and is configured to hook the remote controller 100 on a rack 206 of the sickbed 200, as illustrated in FIG. 10.

Figure 9:
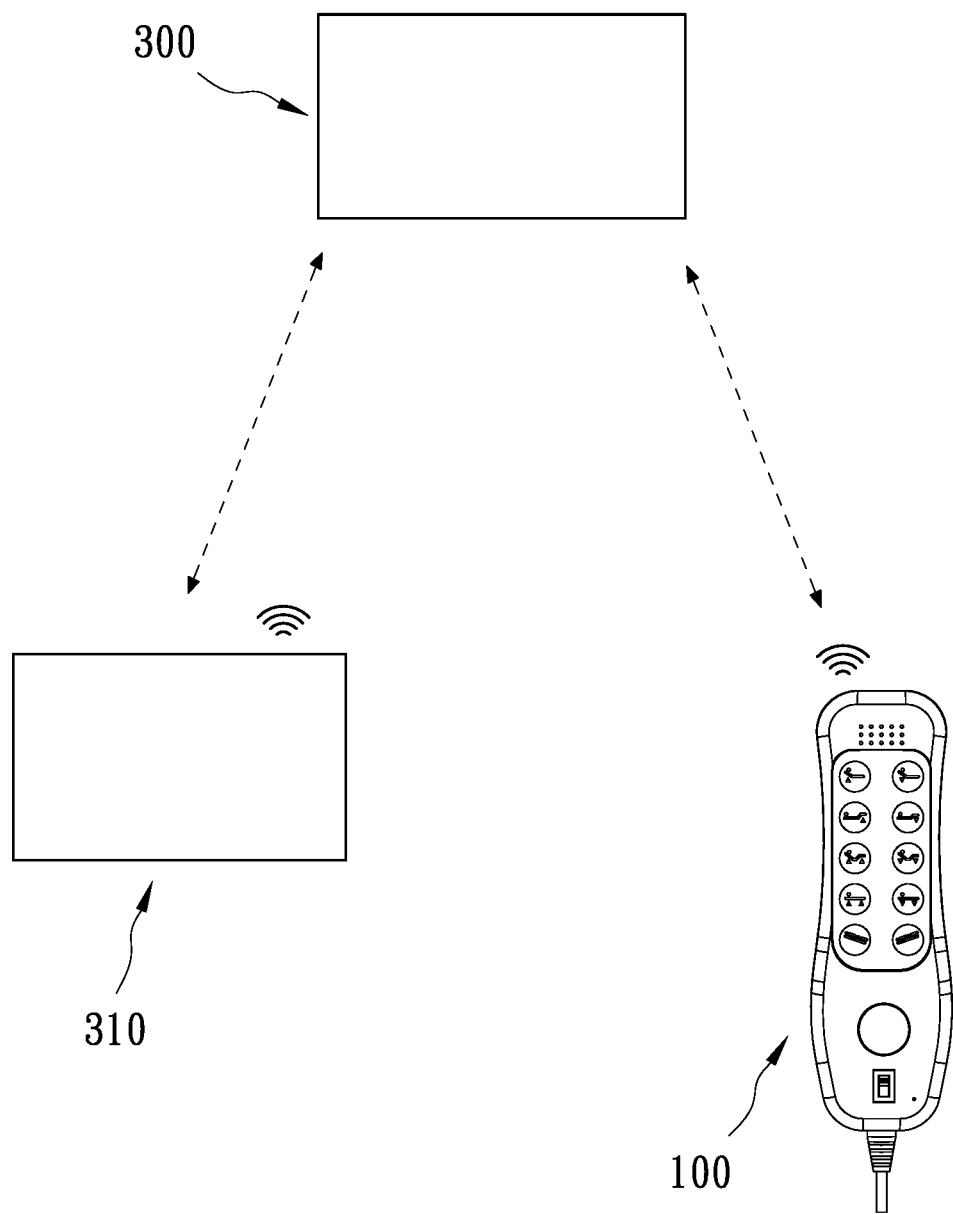
FIG. 9 is a side plan view showing the operation of the remote control for the sickbed according to the preferred embodiment of the present invention.

As shown in FIG. 9, the remote control 100 wirelessly communicates with the remote management platform 310 by using the signal exchanger 300, wherein the signal exchanger 300 has Power Over Ethernet capacity. The remote management platform 310 is configured to make warning or to provide care monitoring to a nursing station of a hospital. Alternatively, the remote management platform 310 is a mobile in which a care monitoring APP program is built so as receive and send the calling signals to the wireless communication module 34, and the remote control 100 and the remote management platform 310 communicate with each other.

With reference to FIGS. 1, 5 and 7, when desiring to lift or descend the sickbed or to adjust an angle of the sickbed, any one of the multiple buttons 210 to 219 is manually pressed so that the microcontroller 32 starts the transmission mechanism 204 to actuate the holding plate 201, the head mounting 202, and the bed end 203 to lift or descend. For example, the button 210 is pressed to lift a user's back and to maintain a user's legs flatly on the sickbed. The button 211 is pressed to descend the user's back and to maintain the user's legs flatly on the sickbed. The button 212 is pressed to lift the user's legs and to maintain the back on the holding plate flatly. The button 213 is pressed to descend the user's legs and to maintain the user's back on the holding plate flatly. The button 214 is pressed to lift the user's back and legs. The button 215 is pressed to descend the user's back and legs. The button 216 is pressed to lift the holding plate 201 completely. The button 217 is pressed to descend the holding plate completely. The button 218 is pressed to maintain a height of a head end of the holding plate higher than a tail end of the holding plate. The button 219 is pressed to maintain a height of the head end of the holding plate lower than the tail end of the holding plate.

When the switch 40 is pushed to abut against the calling knob 33 (as shown in FIG. 1), the locking projection 331 of the calling knob 33 is engaged with the fixing trench 43 of the switch 40, and the first connection portion 45 of the switch 40 is engaged on the first engagement portion 113 of the first casing 11 so that the calling knob 33 is maintained on a locking position and does not generate the calling signal, such that the calling knob 33 is not touched carelessly and does not conduct the power. In the meantime, the speaker 38 makes short warning sounds to indicate that the calling knob 33 is not in an available calling status. When the switch 40 is pushed to move away from the calling knob 33 (as illustrated in FIG. 4), the fixing trench 43 of the switch 40 removes from the locking projection 331 of the calling knob 33, and the second connection portion 46 of the switch 40 is retained on the second engagement portion 114 of the first casing 11, in the meantime, the calling knob 33 is maintained on a starting position and is pressed to conduct the power and to send the calling signal. In this operating mode, the calling knob 33 is pressed to maintain a long-term communication in a long-distance wireless manner and to connect with the mobile (i.e. a smartphone), thus obtaining a care effect of remote calling and instant two-party communication.

When the user starts the calling operation, the microphone 36 records user's audio signals, and the audio signals are calculated by the microcontroller 32, such that the wireless communication module 34 sends the calling signals to the signal exchanger 300 so that the signal exchanger 300 transmits the calling signals to the remote management platform 310, thus receiving the calling signals remotely. When the remote management platform 310 sends the audio signals to the signal exchanger 300 so that the audio signals are sent to the wireless communication module 34 of the remote control 100 via the signal exchanger 300 further, then the audio signals are calculated by the microcontroller 32 and are outputted by the speaker 38, thus obtaining calling effect and two-party communication. The remote control 100 is capable of supporting hands-free phone, emergency call and locally wireless call and realizing one-key calling.

Thereby, the remote control is configured to lift and descent the sickbed and to adjust a using angle of the sickbed by pressing the multiple buttons of the operational panel. Preferably, the remote control is capable of calling caregiver easily and wirelessly by way of the calling knob, the switch, and the care monitoring APP program built in the mobile, thus achieving smart calling and communication among the user, the caregiver, and the user's families.

In addition, the USB connector of the remote control extends out of the power supply set to supply the power to an electric mattress (not shown) of the sickbed. Alternatively, the USB connector is configured to charge the power to the mobile or other low-voltage equipment, thus realizing multiple using purposes.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A remote control for a sickbed, the sickbed including a holding plate and a transmission mechanism, the remote control being electrically connected with the transmission mechanism to control the holding plate to lift or descend, and the remote control communicating with a remote management platform wirelessly; the remote control comprising:
   a body;
   a calling assembly received in the body and including a power supply set, a microcontroller unit, a calling knob, and a wireless communication module which are electrically connected, wherein the microcontroller unit drives and controls the holding plate to lift or descend in a programmable editing manner, the calling knob generates a calling signal, and the calling signal is sent to the remote management platform via the wireless communication module;
   an operational panel located on the body and including multiple buttons electrically connected with the microcontroller, wherein when pressing any one of the multiple buttons, the microcontroller starts the transmission mechanism to actuate the holding plate to lift or descend; and
   a switch arranged on the body and moving close to or away from the calling knob, wherein when the switch is pushed to abut against the calling knob, the calling knob is maintained on a locking position and does not generate the calling signal; when the switch is pushed to move away from the calling knob, the calling knob is maintained on a starting position and is pressed to conduct the power and to send the calling signal.

2. The remote control as claimed in claim 1, wherein the body includes a first casing, a second casing connected with the first casing, and an accommodation chamber defined between the first casing and the second casing; the first casing has a first orifice defined on a first end thereof, a second orifice formed beside the first orifice and communicating with the accommodation chamber with the first orifice, wherein the calling knob is received in the first orifice, and the switch is accommodated in the second orifice.

3. The remote control as claimed in claim 2, wherein the first casing of the body further includes a first engagement portion and a second engagement portion which are formed on two sides of the second orifice and located on an inner fringe of the first casing; the switch includes a U-shaped extension fitted on a side of the calling knob, a straight extension located beside the U-shaped extension, a fixing trench defined on a center of the U-shaped extension, a protruded portion extending from the straight extension and out of the second orifice of the body, and a first connection portion and a second connection portion which are located beside the protruded portion.

4. The remote control as claimed in claim 2, wherein the first casing further includes a first defining groove and s second defining groove which are defined on an inner fringe of the first casing, and the second defining groove is away from the first defining groove.

5. The remote control as claimed in claim 1, wherein the power supply set of the calling assembly has a power cable connected with the transmission mechanism.

6. The remote control as claimed in claim 5, wherein the power supply set has a USB connector configured to connect with the power cable parallelly.

7. The remote control as claimed in claim 1, wherein the calling assembly further includes a microphone drive circuit electrically connected with the microcontroller, a speaker drive circuit electrically connected with the microcontroller, a microphone connected with the speaker drive circuit, and a speaker connected with the speaker drive circuit.

8. The remote control as claimed in claim 1, wherein the wireless communication module of the calling assembly sends the calling signal by using Wi-Fi or Bluetooth.

9. The remote control as claimed in claim 1, wherein the calling knob has a display lamp arranged therein so as to emit lights after the calling knob is pressed.

10. The remote control as claimed in claim 1 further comprising a hook arranged on the body.

\* \* \* \* \*